United States Patent [19]
Eilertsen et al.
[11] Patent Number: 4,543,333
[45] Date of Patent: Sep. 24, 1985

[54] LIQUID PROTEINASE CONCENTRATE AND METHOD FOR PREPARATION

[75] Inventors: Jens H. Eilertsen, Virum; Arne D. Fog, Birkerod; Keith Gibson, Bagsvaerd, all of Denmark

[73] Assignee: Novo Industri A/S, Denmark

[21] Appl. No.: 617,533

[22] Filed: Jun. 5, 1984

[51] Int. Cl.[4] .......... C11D 3/20; C11D 3/32; C11D 3/386; C12N 9/54

[52] U.S. Cl. .......... 435/188; 252/132; 252/153; 252/174.12; 252/544; 252/546; 252/DIG. 12; 435/222

[58] Field of Search .......... 435/188; 252/132, 174.12, 252/153, 546, DIG. 12, 544

[56] References Cited

U.S. PATENT DOCUMENTS

| | | | |
|---|---|---|---|
| 3,050,445 | 8/1962 | Damaskus | 195/63 |
| 3,051,627 | 8/1962 | Bradford | 195/63 |
| 3,296,094 | 1/1967 | Cayle | 435/188 |
| 3,325,364 | 6/1967 | Merritt | 435/188 |
| 3,560,392 | 2/1971 | Eymery | 252/174.12 |
| 3,707,505 | 12/1972 | Maeda | 252/136 |
| 4,305,837 | 12/1981 | Kaminsky | 252/174.12 |
| 4,318,818 | 3/1982 | Letton | 252/174.12 |

FOREIGN PATENT DOCUMENTS

| | | | |
|---|---|---|---|
| 2060485 | 3/1972 | Fed. Rep. of Germany | 252/174.12 |

OTHER PUBLICATIONS

*Research Disclosure*, No. 277, May 1982, p. 170, #21751.

*Primary Examiner*—Dennis L. Albrecht
*Attorney, Agent, or Firm*—Fidelman, Wolffe & Waldron

[57] ABSTRACT

A storage stable liquid enzyme concentrate of *Subtilisin Carlsberg* containing 0.5–6.5 Anson Units of proteinase per gram of concentrate and method for preparing same. Solid form proteinase is extracted with 70–100 parts by volume propylene glycol, 30–0 parts by volume of water, then adjusted as necessary to 60–85% by wt. of the glycol. Stabilizing agents in the concentrate are 0.1–1 mol/Kg of a member selected from the group consisting of Na, K, and Ca glutamates, and glycinates, and acetamide, and also a calcium ion content of 0.04–0.5% by wt., pH range is 5–8.

6 Claims, No Drawings

LIQUID PROTEINASE CONCENTRATE AND METHOD FOR PREPARATION

The present invention relates to aqueous enzyme concentrates adapted for incorporation into liquid detergent formulations.

BACKGROUND OF THIS INVENTION

Incorporation of enzymes, particularly of proteinases into liquid detergent formulations has long been an objective of workers in the detergent arts. A particular difficulty that faced the art has been the rapid decrease of enzyme activity during storage of the liquid detergent product. To a substantial extent, the difficulty has been resolved by the art through inclusion of enzyme stabilizing ingredients such as lower alcohols, calcium ions, and organic acids. (See, for example, the teachings in U.S. Pat. Nos. 4,111,855 and 4,318,818.)

Successful stabilization of proteinase containing detergent formulations imposed upon the producers of the enzyme a requirement to supply enzyme in a form suited to use in the liquid formulations. Desirably, the enzyme supplier should provide a liquid enzyme concentrate adapted to the detergent formulation; indeed, the text of U.S. Pat. No. 4,318,818 appears to indicate that the stabilization system described therein is as applicable to liquid enzyme concentrates as to liquid detergent formulations.

However, the enzyme supplier must be concerned with storage stability of the enzyme concentrate as such, since significant delays can be encountered between preparation of the liquid enzyme concentrate by the enzyme supplier and delivery thereof to the detergent formulator. Both ezyme supplier and detergent formulator would be pleased if the liquid enzyme concentrate exhibited high enough stability to allow also for reasonable delay between delivery of the concentrate and dilution thereof into the detergent formulation without the need for cold storage.

Attention to stabilization of the enzyme concentrate is particularly important in the instance of *Subtilisin Carlsberg,* one industrial form of which is Alcalase ®. Copending Patent Application Ser. No. 448,374, filed Dec. 9, 1982, now U.S. Pat. No. 4,497,897 relates to stabilizing this enzyme in 60–85% by weight propylene glycol, 10–35% water by certain levels of calcium ion and of $C_1$-$C_3$ carboxylate ion. The same subject matter is briefly described in Research Disclosure May 1982, Number 277 at Page 170, #21751.

It has now been discovered that presence of certain $NH_2$ substituted compounds stabilize *Subtilisin Carlsberg.*

BRIEF DESCRIPTION OF THE INVENTION

The present invention comprises a liquid enzyme concentrate of *Subtilisin Carlsberg* containing from 0.5–6.5 Anson Units per gram of concentrate in a solution of propylene glycol and water; the propylene glycol constitutes 60–85% by wt. of the liquid enzyme concentrate and the water constitutes 10–35% by weight of the liquid enzyme concentrate. Preferred is 65–85% propylene glycol; most preferred is 65–80%, water being then 10–30% by wt., and 15–30% respectively.

In addition, $Ca^{++}$ is present as from 0.04–0.5% w/w in the concentrate; preferably 0.04–0.3% by wt., most preferably 0.06–0.15% by wt.

Also present is an $NH_2$ compound selected from the group consisting of acetamide, a glycinate, a glutamate and mixtures thereof, in amounts of from 0.1–1.0 mol/kg. The sodium, potassium, and within the herein specified limits for $Ca^{++}$, the calcium salt of the glycinate or glutamate are contemplated. A mixture of the above-identified $NH_2$ containing compounds may be employed to a cumulative total of up to 1.0 mol/kg of concentrate. Preferred content of $NH_2$ compound is 0.2–0.8 mol/kg, most preferred is 0.3–0.7/kg.

The pH of the concentrate is in the range pH 5–8, and preferably is pH 6–7.

DETAILED DISCUSSIONS OF THE INVENTION

As has been indicated, the *Subtilisin Carlsberg* of this invention is intended for dilution into liquid detergent formulations, forming from about 0.25%–2% of the final formulation, more usually from 0.5–1%. The detergent formulation per se forms no part of this invention. Normally, the proteinase concentrate of this invention will be supplied to soapers, who will incorporate the concentrate into their own preferred liquid detergent formulation as the proteinase component thereof.

For example, the liquid proteinase concentrate of this invention may be employed with the detergent formulation materials in the general proportions described in U.S. Pat. No. 4,318,818.

Although considerable attention has been paid to proteinase containing liquid detergents and the need for stablizing the enzyme therein, relatively little attention has been paid to the need for stabilization of the liquid enzyme concentrates supplied to the soapers. One of the proteases most commonly employed in detergents, namely, *Subtilisin Carlsberg* for which an exemplary trade name is Alcalase ® loses activity rapidly in aqueous solution concentrate form.

In addition, relatively little attention has been paid to how to prepare stable liquid form proteinase concentrates. That is not to say, however, that this invention occupies a vacant space in the art. Prior workers in the art have recognized the rapid activity loss exhibited by proteinase in aqueous solutions and that the activity loss be described substantially by presence of polyhydric alcohols, including propylene glycol, vide, for example, U.S. Pat. No. 3,717,550 and Belgium Pat. No. 773,893 teachings. However, none of the prior art suggest the present composition, nor the ease with which the liquid proteinase concentrates of this invention can be prepared from the solid form enzyme concentrate products that result from state-of-the-art fermentation and enzyme recovery techniques. This solid form proteinase concentrate product may contain a substantial mount of water e.g., up to around 50% w/w.

To prepare the liquid proteinase concentrate, the procedure described in Research Disclosure, December 1981, Number 212, at Pp. 451–452 may be followed. The solid form enzyme concentrate in activity quantities sufficient to generate the desired final activity of 0.5–6.5 Anson Units per gram of liquid concentrate, preferably 2–4 Anson Units per gram of liquid concentrate, more preferably 2–3 Anson Units per gram of liquid concentrate, is extracted with a 70–100/30–0 by volume mixture of propylene glycol and water. The extractant may be 100% propylene glycol. The resulting slurry is filtered or centrifuged to remove undissolved solids.

The filtrate/supernatant may be the finished concentrate of this invention if the propylene glycol-water mixture had been doped appropriately with the $NH_2$ compound and calcium ion beforehand, and the propylene glycol-water mixture employed causes the extact to be within the by weight proportions thereof described above for the liquid proteinase concentrate.

The pH of the liquid proteinase concentrate will ordinarily be in the desired pH 5-8 range, but pH adjustment as necessary, before and/or after inclusion of the enzyme into the propylene glycol-water mixture is contemplated. Addition of the $NH_2$ compound and of calcium ions to the propylene glycol-water mixture before or after inclusion of the enzyme therein is also contemplated.

Essentially, all of the proteinase is taken up in solution in the liquid, along with some non-enzymatic materials. Propylene glycol-water mixtures with a propylene glycol content of more than 70 parts of glycol to less than 30 parts of water (parts by volume) seems to be the superior extractant vis a vis the other alcohols suggested to the art, and vis a vis lower propylene glycol content mixtures.

In total, the liquid enzyme concentrate contains the below listed ingredients in the below-given preferred proportions.

(1) Enzymatic activity corresponding to 2–3 Anson Units/g solution;
(2) Some non-enzymatic material from the solid form proteinase concentrate in an amount of around 0.005–0.05 g/g solution;
(3) A solvent which is a mixture of propylene glycol 1,2 and water in an amount of 60–85% by wt. and 10–35% by wt., respectively, in regard to the liquid enzyme concentrate;
(4) Additives according to the below-indicated Table.

TABLE 1

| Ionic Additive | Exemplary Counter Ion | Concentration of Ionic Additive |
|---|---|---|
| $Ca^{++}$ | $Cl^-$, $NO_3^-$ | 0.04–0.5% w/w |
| $^-OOCCHNH_2CH_2CH_2COO^-$ | $Na^+$, $K^+$, $Ca^{++}$ | 0.1–1.0 mol/kg |
| $CH_3CONH_2$ | — | 0.1–1.0 mol/kg |
| $NH_2CH_2COO^-$ | $Na^+$, $K^+$, $Ca^{++}$ | 0.1–1.0 mol/kg |

Only one of the three $NH_2$ compound additives need be added, although more than one may be present. If more than one of the three $NH_2$ compound additives are added, the maximum sum of their concentrations is about 1.0 mol/kg. Since the $Ca^{++}$ concentration for stabilization is only about 0.01–0.13 mol/kg, the molar proportions of calcium ion to glycinate or glutamate ion is usually insufficient to allow calcium glycinate or glutamate to satisfy requirements for both the calcium and the counter ion.

For further understanding of the present invention, the following specific Example is presented.

EXAMPLE

In all runs in this Example, the enzyme starting material was ALCALASE concentrate produced in accordance with the teachings appearing in Belgium Pat. No. 889,336 which concentrate, however, was not subjected to the final drying operation. One part of this protease starting material (for the sake of brevity in the following referred to as S) was suspended in two parts of propylene glycol, and the pH value was adjusted to 6.5±0.5. The suspension was stored at ambient temperature for three days and then filtered. Subsequently, $CaCl_2$ and either acetamide or sodium formate or sodium acetate or propionic acid or glycine or glutamic acid where added in such amounts as to generate the concentrations indicated in Table 2A below, the pH value was adjusted to 6.4 vide Table 2A, with 80% acetic acid or 12% NaOH, as the case may be. Finally, the liquid was germ filtered.

The enzyme stability test data for the final liquids of the above-described run are provided in Tables 2B and 2C below, and the appearance-stability of the final liquid concentrates are provided in Table 2D.

TABLE 2A

| Sample | Water % w/w | Fatty Acid Residue or Alternative Stabilizer | Mol/kg | Calcium as % w/w Ca | pH | Activity AU/g |
|---|---|---|---|---|---|---|
| 38A | 18.3 | Formate | 0.35 | 0.09 | 6.4 | 2.16 |
| 38B | 20.1 | Acetate | 0.35 | 0.10 | 6.4 | 2.17 |
| 38C | 18.5 | Acetamide | 0.50* | 0.08 | 6.4 | 2.15 |
| 38E | 19.2 | Glycinate | 0.50* | 0.08 | 6.4 | 2.27 |
| 38F | 21.7 | Propionate | 0.45 | 0.10 | 6.4 | 2.05 |
| 38J | 20.8 | L-glutamate | 0.50* | 0.07 | 6.4 | 2.32 |
| 38N | 20.7 | L-glutamate | 0.25* | 0.08 | 6.4 | 2.27 |

*From amount added

TABLE 2B

| | Storage at 37° C.; % Activity Remaining After (Weeks) | | | | | | | |
|---|---|---|---|---|---|---|---|---|
| Sample | 2 | 4 | 7 | 10 | 16 | 26 | 39 | 52 |
| 38A | 99 | 97 | 92 | 96 | 90 | 86 | 75 | 69 |
| 38B | 92 | 93 | 92 | 87 | 83 | 74 | 63 | 56 |
| 38C | 100 | 95 | 88 | 86 | 80 | 71 | 62 | 53 |
| 38E | 99 | 90 | 89 | 87 | 82 | 71 | 67 | 59 |
| 38F | 98 | 93 | 87 | 85 | 78 | 72 | 55 | 49 |
| 38J | 98 | 96 | 93 | 80 | 86 | 80 | 76 | 67 |
| 38N | 98 | 93 | 80 | 92 | 88 | 77 | 74 | 65 |

TABLE 2C

| | Storage at 25° C.; % Activity Remaining After (Weeks) | | | |
|---|---|---|---|---|
| Sample | 16 | 26 | 39 | 52 |
| 38A | 101 | 93 | 95 | 94 |
| 38B | 99 | 94 | 94 | 91 |
| 38C | 101 | 97 | 100 | 93 |
| 38E | 99 | 93 | 99 | 93 |
| 38F | 99 | 98 | 83 | 93 |
| 38J | 101 | 98 | 89 | 97 |
| 38N | 102 | 97 | 99 | 93 |

TABLE 2D

| Sample | Appearance After 7 Weeks at 37° C. |
|---|---|
| 38A | OK, i.e., clear and no precipitate |
| 38B | OK, i.e., clear and no precipitate |
| 38C | OK, i.e., clear and no precipitate |
| 38E | OK, i.e., clear and no precipitate |
| 38F | Clear, slight precipitate |
| 38J | OK, i.e., clear and no precipitate |
| 38N | OK, i.e., clear and no precipitate |

The foregoing Example demonstrates that the stability of the liquid proteinase concentrate is excellent.

We claim:

1. A liquid enzyme concentrate comprising:
the proteinase of *Subtilisin Carlsberg* in concentration of from 0.5–6.5 Anson Units per gram of concentrate;
propylene glycol in an amount of 60–85% and water in an amount of 10–35% by wt.;

calcium ion in concentration of about 0.04–0.5% by wt.;

acetamide in concentration of about 0.1–1.0 mol/kg, the pH being in the range of 5–8.

2. The concentrate of claim 1 wherein the concentration of acetamide is in the range of 0.2–0.7 mol/kg.

3. The concentrate of claim 1 wherein the pH of the concentrate is in the range of 6–7.

4. The concentrate of claim 1 wherein the enzyme concentration is in the range of 2–4 Anson Units per gram.

5. The concentrate of claim 1 wherein the calcium ion content is in the range of 0.06–0.15% by wt.

6. The concentrate of claim 1 wherein the propylene glycol content is 65–80% by wt. and the water content is 15–30% by wt.

* * * * *